United States Patent [19]

Burton et al.

[11] Patent Number: 5,475,006

[45] Date of Patent: Dec. 12, 1995

[54] EXTENSIVELY OXIDIZED DERIVATIVES OF CAROTENOIDS, RETINOIDS AND RELATED CONJUGATED POLYENES USEFUL AS NON-TOXIC CELL-DIFFERENTIATION INDUCERS, ANTI-PROLIFERATIVE AGENTS, AND ANTI-TUMOR AGENTS

[75] Inventors: Graham Burton, Orleans; Janusz Daroszewski, Gloucester; Jenny Phipps, Ottawa, all of Canada

[73] Assignee: National Research Council of Canada, Ottawa, Canada

[21] Appl. No.: 288,315

[22] Filed: Aug. 10, 1994

[51] Int. Cl.⁶ .......................... A01N 43/00; A61K 31/47
[52] U.S. Cl. .................. 514/310; 560/303; 568/347; 568/351
[58] Field of Search .................. 514/310; 560/303; 568/347, 351; 424/439

[56] References Cited

U.S. PATENT DOCUMENTS

| | | | |
|---|---|---|---|
| 4,105,855 | 8/1978 | Schulz et al. | 560/190 |
| 4,127,455 | 11/1978 | Schulz et al. | 204/78 |
| 5,097,063 | 3/1992 | Moldt | 560/303 |
| 5,225,604 | 7/1993 | Moldt | 568/347 |
| 5,310,554 | 5/1994 | Haigh | 424/439 |
| 5,358,915 | 10/1994 | Nebergall et al. | 502/27 |

OTHER PUBLICATIONS

R. Peto et al, "Can Dietary Beta–Carotene . . . Cancer Rates", *Nature*, (1981), 290, 201–208.
N. Krinsky, "Actions of Carotenoids . . . Systems", *Annu. Rev. Nutr.*, 13, 561–587, (1993).
D. Hill et al, "Retinoids and Cancer Prevention", *Annu. Rev. Nutr.*, 12, 161–181, (1992).
Burton et al, "β–Carotene . . . Antioxidant", *Science*, 224, 569–573, (1984).
Mordi et al, "Exploration Study . . . Autoxidation", *Tetrahedron Letters*, 32(33), 4203–4206, (1991).
Mordi et al, "Oxidative Degradation . . . –Carotenal", *Tetrahedron*, 49(4), 911–928, (1993).
Alaoui–Jamali et al, "In Vivo Reversal . . . Analog RO11–29331", *J. Pharmacol. Exp. Ther.*, 264(3), 1299, (1993).

*Primary Examiner*—Arthur C. Prescott
*Attorney, Agent, or Firm*—Juliusz Szereszewski

[57] ABSTRACT

β-Carotene and canthaxanthin, as representative carotenoids, and to a lesser extent, retinoic acid, a representative retinoid, undergo extensive oxidation to yield substances, insofar as oxidized β-carotene is a model, which have properties useful as non-toxic agents active against cell proliferation, tumors, and tumorigenic viruses, and useful as promoters of cell differentiation. It is evident from chemical analysis of the highly oxidized β-carotene product mixture that none of the various forms of vitamin A are present or are present only in minor amounts. Furthermore, the biological activities of oxidized canthaxanthin and retinoic acid, which cannot form, vitamin A, indicate the presence of active substances that are different from vitamin A. Although the anti-proliferative and differentiation promotion activities of oxidized β-carotene resemble those of vitamin A itself, generally the effects are more powerful for oxidized β-carotene in a wide variety of circumstances. Unlike vitamin A, the oxidized β-carotene of the invention is non-toxic.

11 Claims, 14 Drawing Sheets

EXTENSIVELY OXIDIZED DERIVATIVES OF CAROTENOIDS, RETINOIDS AND RELATED CONJUGATED POLYENES USEFUL AS NON-TOXIC CELL-DIFFERENTIATION INDUCERS, ANTI-PROLIFERATIVE AGENTS, AND ANTI-TUMOR AGENTS

FIELD OF THE INVENTION

This invention relates to carotenoid, retinoid and related conjugated polyene derivatives with cell-differentiation-inducing, anti-proliferative and anti-tumor properties, useful as chemotherapeutic and chemopreventive agents, and more particularly, to such derivatives obtained by extensive oxidation of carotenoids, retinoids and related conjugated polyenes.

BACKGROUND OF THE INVENTION

Carotenoids and retinoids are naturally occurring substances which contain extensively conjugated polyene chains. Carotenoids have the most extensively conjugated systems of carbon-carbon double bonds which give rise to their many varied and brilliant colors. Many carotenoids and retinoids, which are naturally occurring substances, are biologically active. For example, certain hydrocarbon members of the carotenoid family (most notably, β-carotene, or pro-vitamin A, one of the most abundant carotenoids in food) are sources of retinol (one form of vitamin A); carotenoids protect plants from photosensitized oxidative damage, probably by deactivating singlet oxygen; epidemiological evidence indicates that carotenoid intake correlates inversely with the incidence of some types of cancer (Peto et al, Nature, 1981, 290, 201–208). Carotenoids and retinoids have been shown to retard the development of some experimentally induced animal tumors (N. I. Krinsky. Actions of Carotenoids in Biological Systems, Annu. Rev. Nutr, 13, 561–587 (1993); Matthews-Roth, Curr. Top. Nutr. Dis. [New Prot. Roles Select. Nutr.], 1989, 22, 17–38; Pure Appl. Chem., 1985, 57, 717– 722); a number of dietary intervention studies are being carried out to try to determine the efficacy of supplemental β-carotene as a non-toxic, dietary anti carcinogen that can effectively decrease cancer mortality and most recently the possibility has begun to be examined that β-carotene may be associated with decreased incidence of coronary heart disease; recent clinical data with the use of related compounds (retinoids—retinoic acid, retinol and retinamides) have demonstrated a role in anti-cancer therapy, both as a therapeutic and a preventive agent (cancers of the skin, head and neck, lung and bladder, acute promyelocytic leukemia, leukoplakia and myelodysplastic syndromes; D. L. Hill and C. J. Grubs, Retinoids and Cancer Prevention, Annu. Rev. Nutr. 1992, 12, 161–181); and finally, β-carotene has antioxidant properties at the low oxygen pressures found in tissues (Burton and Ingold, β-Carotene: an unusual type of lipid antioxidant, Science, 1984, 224, 569–573).

Carotenoids, retinoids and related conjugated polyenes are reactive towards molecular oxygen ($O_2$) and may therefore be oxidatively degraded in foodstuffs during storage, even at reduced temperatures. Carotenoids are more reactive than retinoids towards oxygen because of their larger, more extensively conjugated system of double bonds. The products of such oxidative degradation of carotenoids retinoids, and related conjugated polyenes and their potential physiological activities have, nevertheless, received remarkably little attention, with the exception of vitamin A, which is obtained as a product of the biological oxidation of β-carotene.

Mordi et al, Exploratory study of β-carotene Autoxidation, published in Tetrahedron Letters, 1991, 32 (33), 4203–4206, examined the products formed during the self-initiated autoxidation of β-carotene. The paper concludes that the main products identified in the early stages of β-carotene autoxidation are epoxides, β-ionone, β-apo-13-carotenone, retinal, and related carbonyl compounds; in the final mixture, short chain carbonyl compounds predominate.

Another paper by Mordi et al, "Oxidative Degradation of β-carotene and β-Apo-8'-carotenal", published in Tetrahedron Vol. 49, No. 4, pp. 911–928, Jan. 22, 1993, shows that self-initiated oxidation of β-carotene with molecular oxygen produces epoxides, dihydrofurans, carbonyl compounds, carbon dioxide, traces of alcohols, and some other compounds. The paper, co-authored by one of the present inventors, also makes a mention of some polymeric/oligomeric material which frequently deposited out of solution, particularly in the later stages of β-carotene oxidation. The properties of the polymer/oligomer are not disclosed in the paper.

This patent application results from the development of our idea that the biological activity of carotenoids derives not from the carotenoids themselves but instead from one or more of their oxidation products generated in vivo. Retinoids are also included because of their ability to oxidize, although not as readily as carotenoids. The biological activity of oxidized retinoids is distinct from the known activity of the retinoids themselves.

SUMMARY OF THE INVENTION

It has been found that mixtures obtained by oxidation of β-carotene, canthaxanthin or retinoic acid with oxygen, $O_2$, under conditions in which at least some of the substrate reacts, on a molecular basis, with a several-fold greater amount of oxygen (a process hereinafter referred to as extensive oxidation) are able, in a cell culture, to induce cancer-derived and virally-transformed cells to proliferate less rapidly in a manner that is non-toxic to normal cells. Furthermore, it has been determined in several of the treated cell lines that cell differentiation occurs, i.e., the cancer-like cells eventually acquire many of the characteristics of normal cells. It has also been found that the mixture of material obtained from extensively oxidized β-carotene is able to retard or arrest, in a non-toxic manner, the growth of tumors in mice.

It is proposed to oxidize carotenoids, retinoids or related conjugated polyenes with oxygen in conditions effective to obtain a mixture containing an oligomeric or polymeric component.

The oxidation can be carried out with oxygen and a carotenoid, retinoid or conjugated polyene, either in the solid state or dissolved in an organic solvent.

Based on laboratory tests as described below, both the oxidized mixtures and the oligomeric/polymeric component obtained upon oxidation of β-carotene, canthaxanthin, retinoic acid and partially oxidized mixtures thereof are believed to be effective as anti-proliferative and anti-tumor agents and differentiation inducers.

The structural formulae of the polymeric ingredients have not been determined thus far. There is evidence that the polymers formed upon oxidation of β-carotene, canthaxanthin or retinoic acid have a polyperoxide structure and contain acidic groups.

To address the question of the substances of the present invention occurring in nature, it will be appreciated that formation of polymeric components during oxidation is likely to be retarded in nature as non-isolated carotenoids and retinoids are protected against oxidation by antioxidants such as vitamin E. However, a polar material (which polymerized upon isolation), obtained by oxidizing β-carotene in the presence of vitamin E in solution, was as active in in vitro cell culture tests as the polymeric material obtained in the uninhibited oxidation.

The molecular weight of much of the polymeric component of the mixture of the invention is relatively low compared to the molecular weights of carotenoids and retinoids. For this reason, the material can be termed an oligomer as well as a polymer. For the purpose of the instant specification, the term polymer, or polymeric, will be used to define the material.

6a—fraction 1

6b—fraction 2,

6c—fraction 3, and

Figure 7:
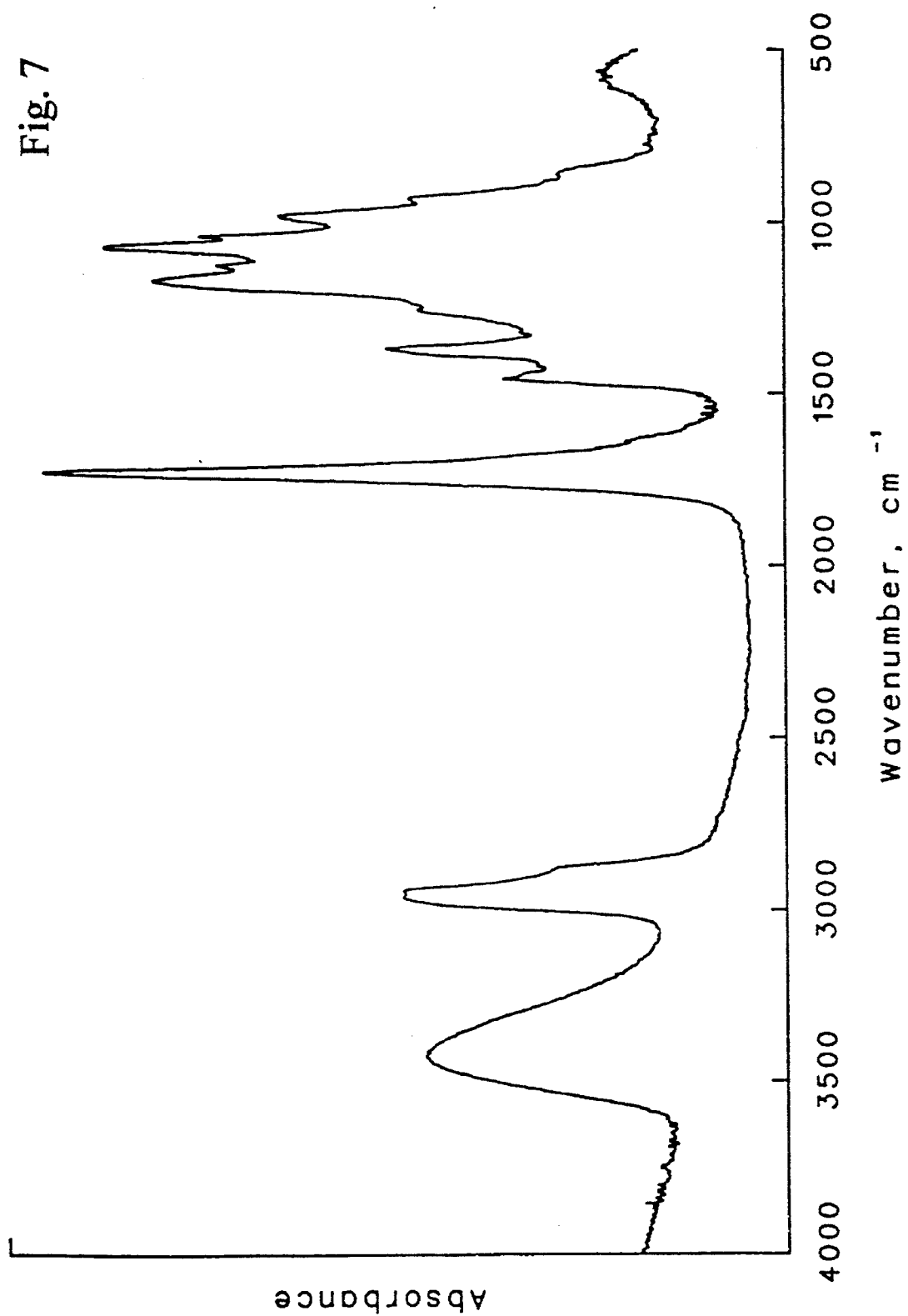
Figure 8:
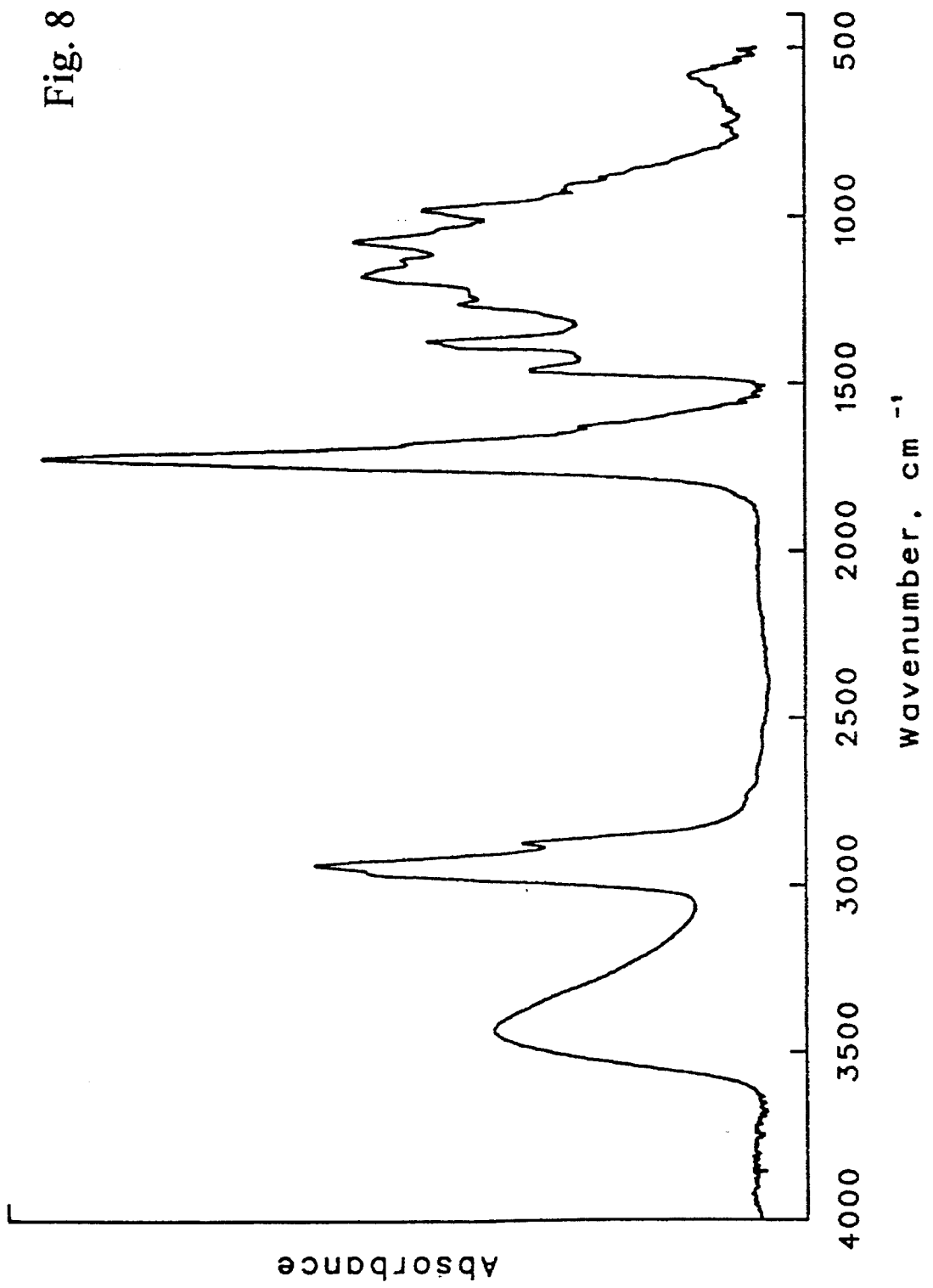
Figure 9:
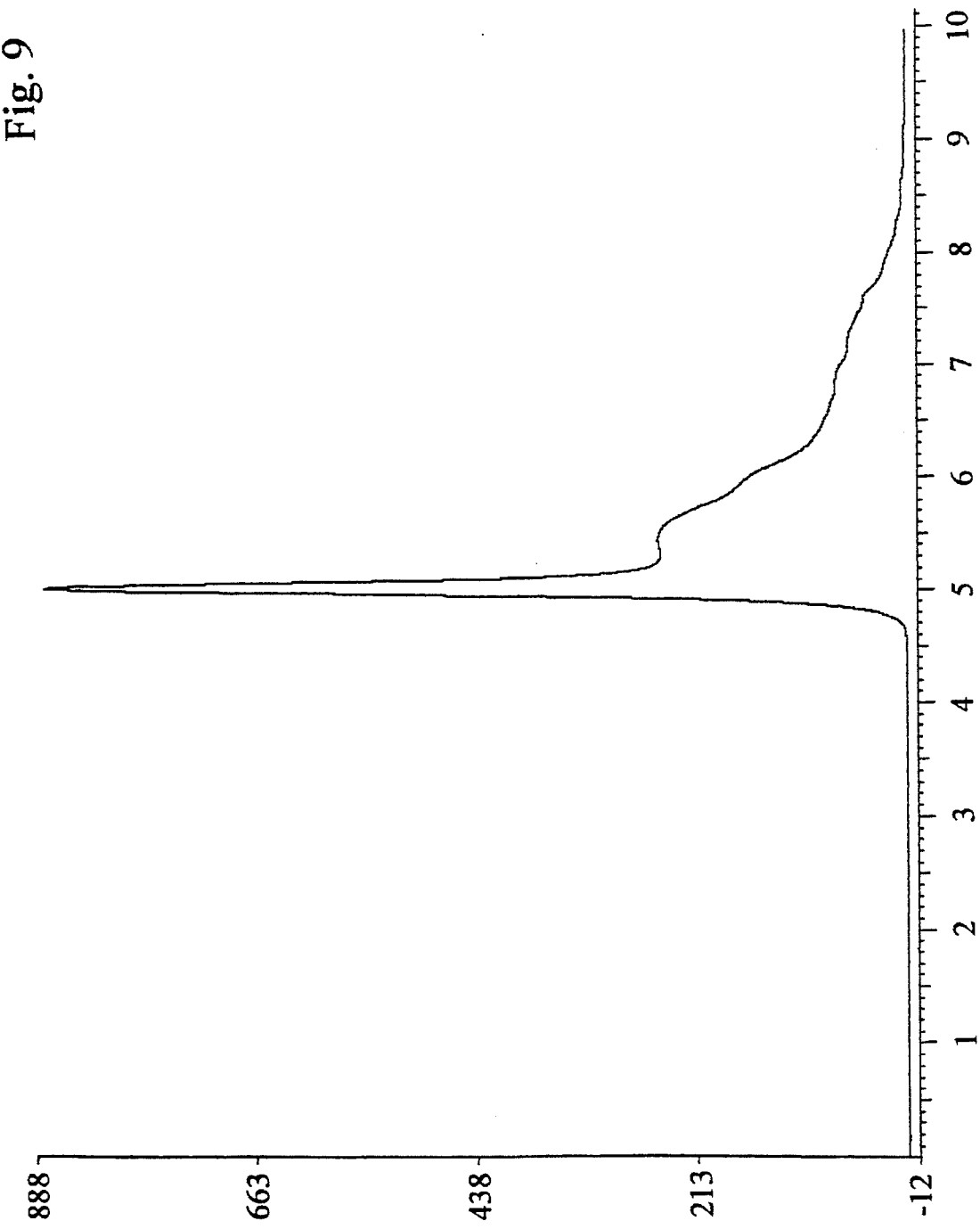

6d—fraction 4;

FIG. 7 represents the FTIR spectrum of fraction 1 of the polymeric mixture,

FIG. 8 illustrates the FTIR spectrum of the material obtained by oxidation of solid β-carotene, FIG. 9 illustrates the results of GPC analysis of the polymeric material obtained by oxidation of solid β-carotene, FIGS. 10a–10f (photographs) illustrate the effect of retinoic acid and extensively oxidized β-carotene on differentiation of ES cells as follows:

FIG. 10a—ES cells, no inducer

Figure 10:
Figure 10B:
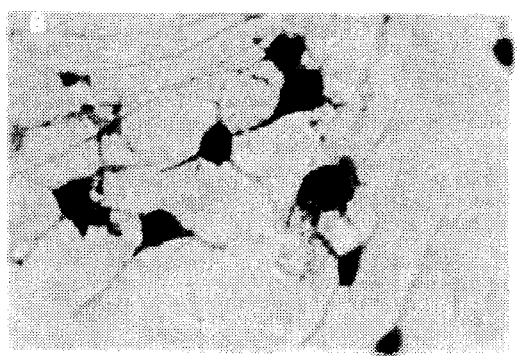

FIG. 10b—retinoic acid

Figure 10C:
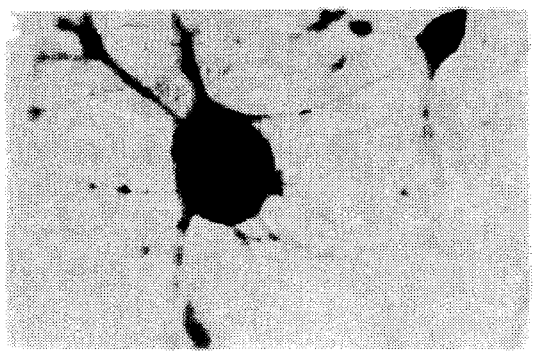

FIG. 10c—extensively oxidized β-carotene 3 µM

Figure 10D:

FIG. 10d—extensively oxidized β-carotene 7.5 µM

Figure 10E:

FIG. 10e—extensively oxidized β-carotene 15 µM

Figure 10F:
Figure 11:
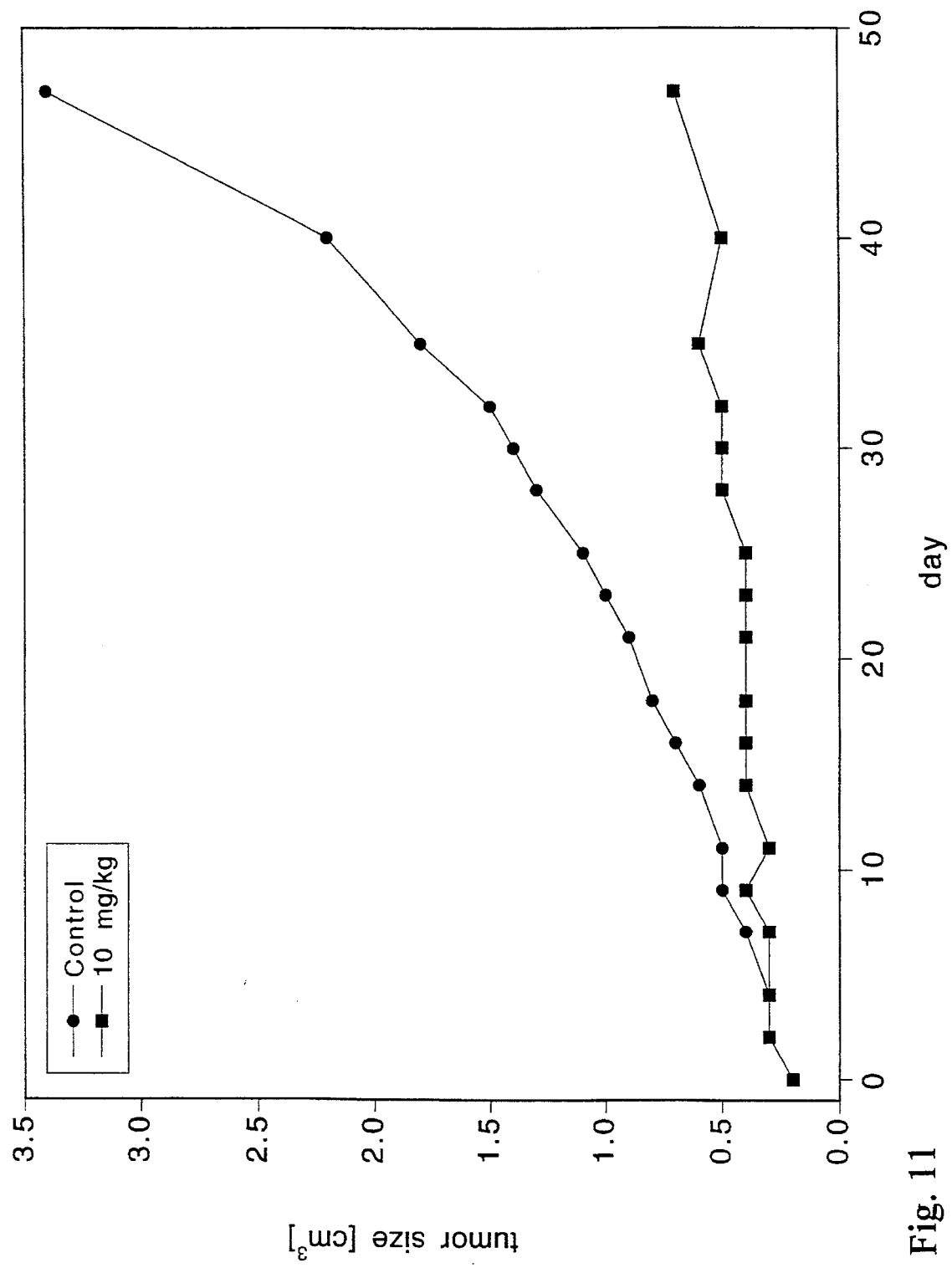
Figure 12:
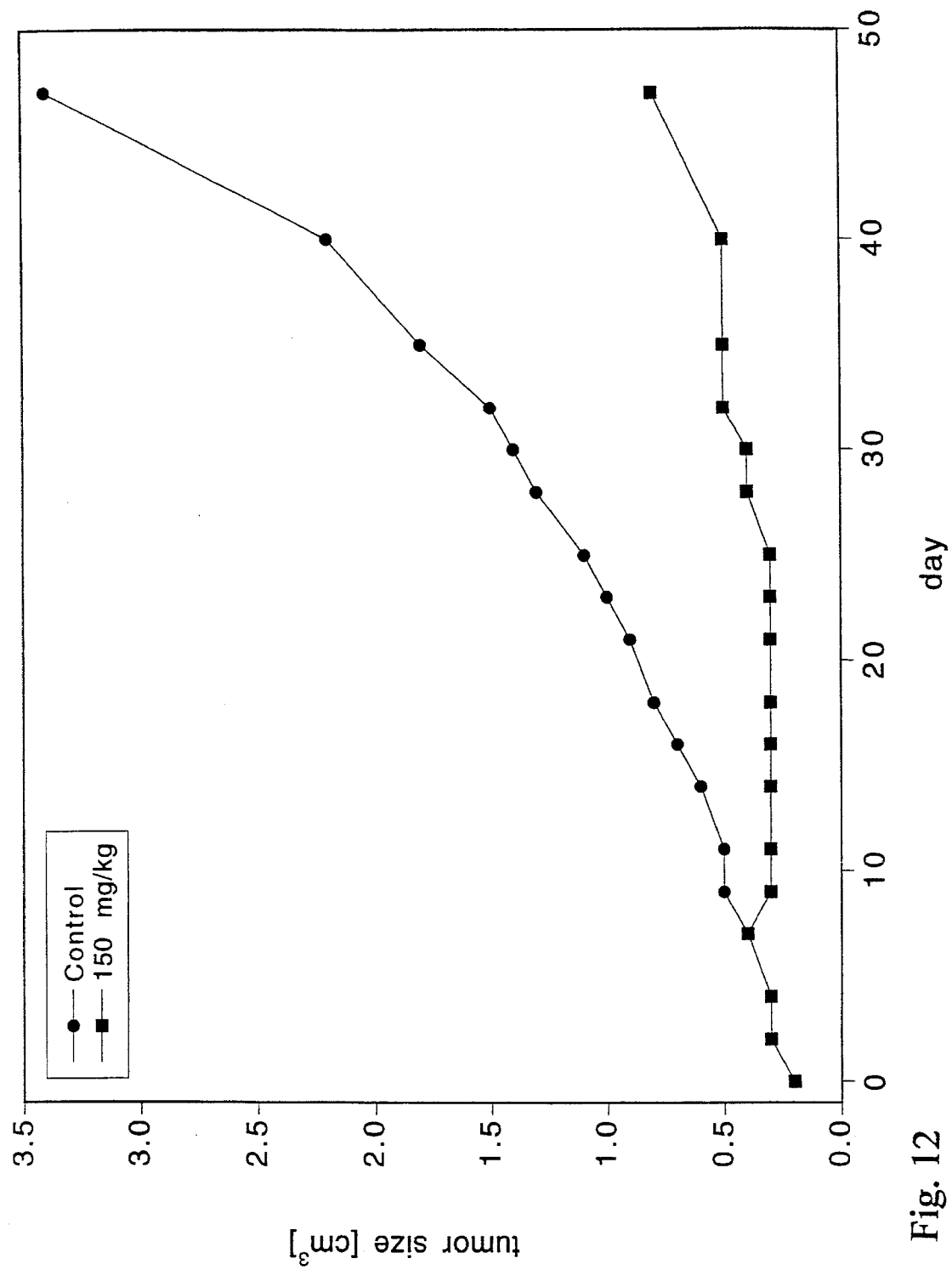
Figure 13A:
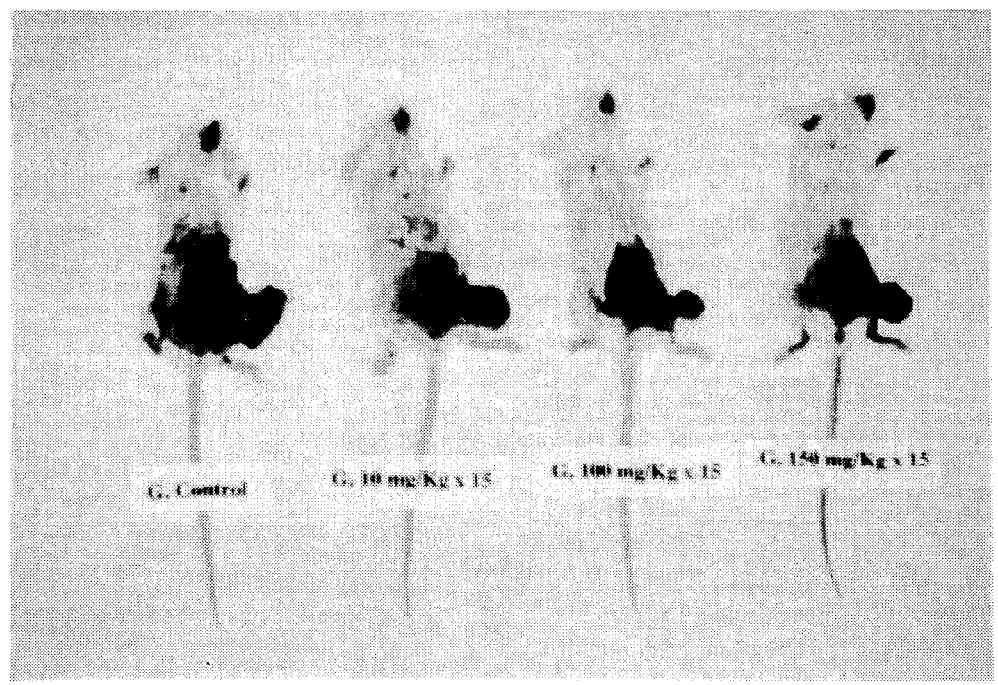
Figure 13B:
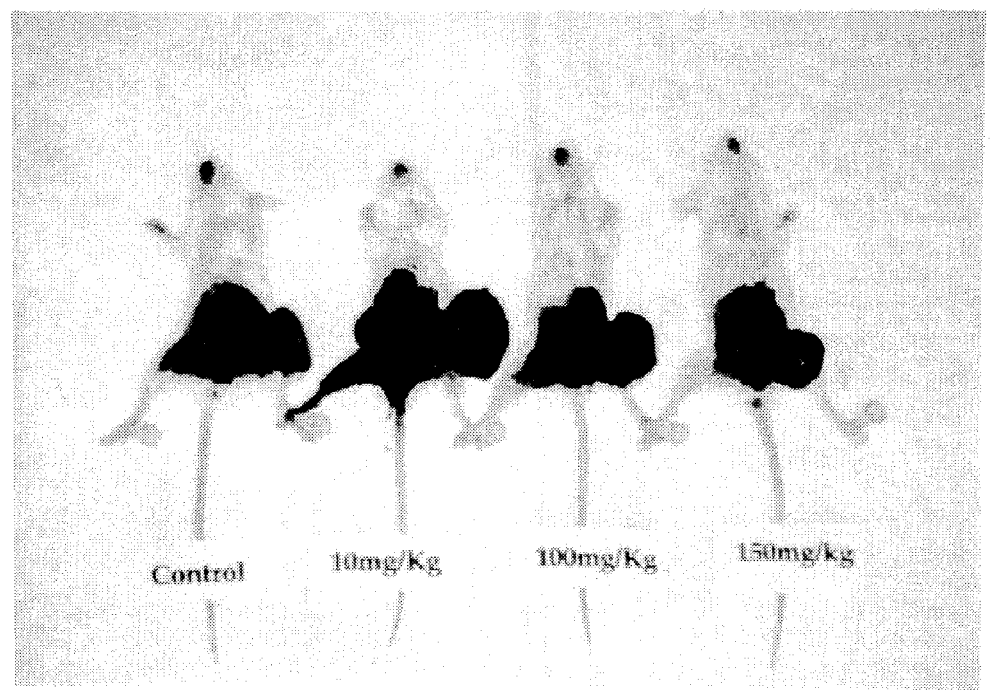

FIG. 10f—extensively oxidized β-carotene 30 µM;

FIG. 11 illustrates the effect of extensively oxidized β-carotene on tumor growth at dose of 10 mg/kg injected on days 0,2,4,7,9,11,14,16 and 18, FIG. 12 illustrates the effect of extensively oxidized β-carotene on tumor growth at dose of 150 mg/kg injected on days 0,2,4,7,9,11,14,16 and 18, FIG. 13a illustrates the effect of extensively oxidized β-carotene on tumor size in sacrificed animals which had been treated with different doses of extensively oxidized β-carotene and the control (untreated animal) and FIG. 13b illustrates the effect of extensively oxidized β-carotene on tumor size in sacrificed animals which had been treated with different doses of extensively oxidized β-carotene and developed hemorrhaging around the tumors and the control (untreated animal).

DETAILED DESCRIPTION OF THE INVENTION

β-Carotene, retinoic acid and related compounds have been identified as potential anti-cancer agents or even used as preventive and/or therapeutic agents in the treatment of different forms of cancer e.g. lung cancer and some forms of leukemia. The chemopreventive action of β-carotene has also received some attention in connection with the mode of action of vitamin A (retinoic acid), itself an oxidation product of β-carotene. Vitamin A has been shown to be capable of causing some types of cancer cells to at least partly revert from their proliferative, embryonic-like state to that resembling normal cells. However, the severe toxicity of vitamin A strictly limits its therapeutic applications.

The mechanism by which the carotenoids act is not yet understood. The actions of vitamin A itself and related retinoids which affect cell growth and differentiation appear to be mediated via the retinoid receptors located at the cell nucleus.

Regarding β-carotene and possibly other carotenoids, it has been widely believed but not proven that its anti-cancer effects derive somehow from the anti-oxidant properties of the intact molecule and not from its ability to form vitamin A.

Isolated β-carotene and other carotenoids readily undergo spontaneous oxidation by reaction with oxygen in air. Retinoids also are capable of undergoing spontaneous oxidation. However, it is appreciated from the outset that the presence of fewer conjugated olefinic bonds in retinoids diminishes the rate and extent of their spontaneous oxidation.

Spontaneous oxidation may cause carotenoids and retinoids to behave in vivo as intracellular pro-oxidants, acting as sources of biologically active radicals and/or radical-derived products. Free radicals and products of free radical oxidation have been recognized to act as secondary messengers playing a significant role in the signalling pathways of living cells. Indeed, although it has been recognized for a long time that the production of free radicals is an inevitable consequence of life in an aerobic environment and this was generally regarded as harmful to cells, more recently there has been a growing appreciation that free radicals, particularly oxy-radicals, play an important role in the maintenance, control and development of cells.

It is our discovery that the products of extensively oxidized carotenoids, retinoids and related conjugated polyenes and their structural analogs, possess non-vitamin A bioactivity. We have demonstrated this by extensively pre-oxidizing β-carotene, canthaxanthin and retinoic acid in vitro and testing the mixture of oxidation products for biological activity. It is important to recognize the distinction between the products of extensive oxidation, which are the basis of the present invention, from vitamin A which is the well-known product of the in vivo oxidative conversion of β-carotene and other vitamin A-yielding carotenoids.

To validate the present invention, in vivo and in vitro biological tests were conducted, and methods of synthesis and analytical data on the oxidation mixtures of β-carotene, canthaxanthin and retinoic acid are set forth hereinbelow.

EXPERIMENTAL

β-Carotene, canthaxanthin and retinoic acid were oxidized as described below:

Example 1: Oxidation of b-carotene

A 20 mM solution of β-carotene (Fluka) in benzene saturated with oxygen was incubated in a shaker bath, in the dark, at 30° C. under pure oxygen at atmospheric pressure. After 72 hours, when 6 to 8 molar equivalents of oxygen had been consumed, the solvent was evaporated to give a resin-like, yellow residue.

Effect of solvent:

Oxidation of β-carotene in carbon tetrachloride yielded results essentially identical to those obtained in benzene.

Quantity of vitamin A formed:

Neither retinol nor retinoic acid, both products of the in vivo, enzymatic oxidation of β-carotene, were detected in the oxidation mixture. Although retinal, which can be oxidized to retinoic acid, has been identified as a product it is present in too small amount to account for the biological activity of the oxidized b-carotene mixture. Furthermore, the biological activity of the oxidized mixture differs substantially from that of vitamin A, as will be described below.

Polymeric Materials:

Very substantial amounts of polymeric substances are formed during the oxidation (see below). It is likely, by analogy with the oxidation reactions of other olefinic compounds, that the higher molecular weight substances correspond to polymers made up of oxidized β-carotene fragments. Various concentrations of β-carotene were tested to determine the dependence of polymerization upon the concentration of β-carotene in solution. 20 mM, 2 mM and 0.2 mM solutions of β-carotene in benzene, saturated with oxygen, were incubated under pure oxygen (760 mm Hg) at 30° C. in the dark. The polymeric ingredient was the main product in all cases. Furthermore, the polymeric ingredient forms early in the oxidation of b-carotene.

Figure 1:
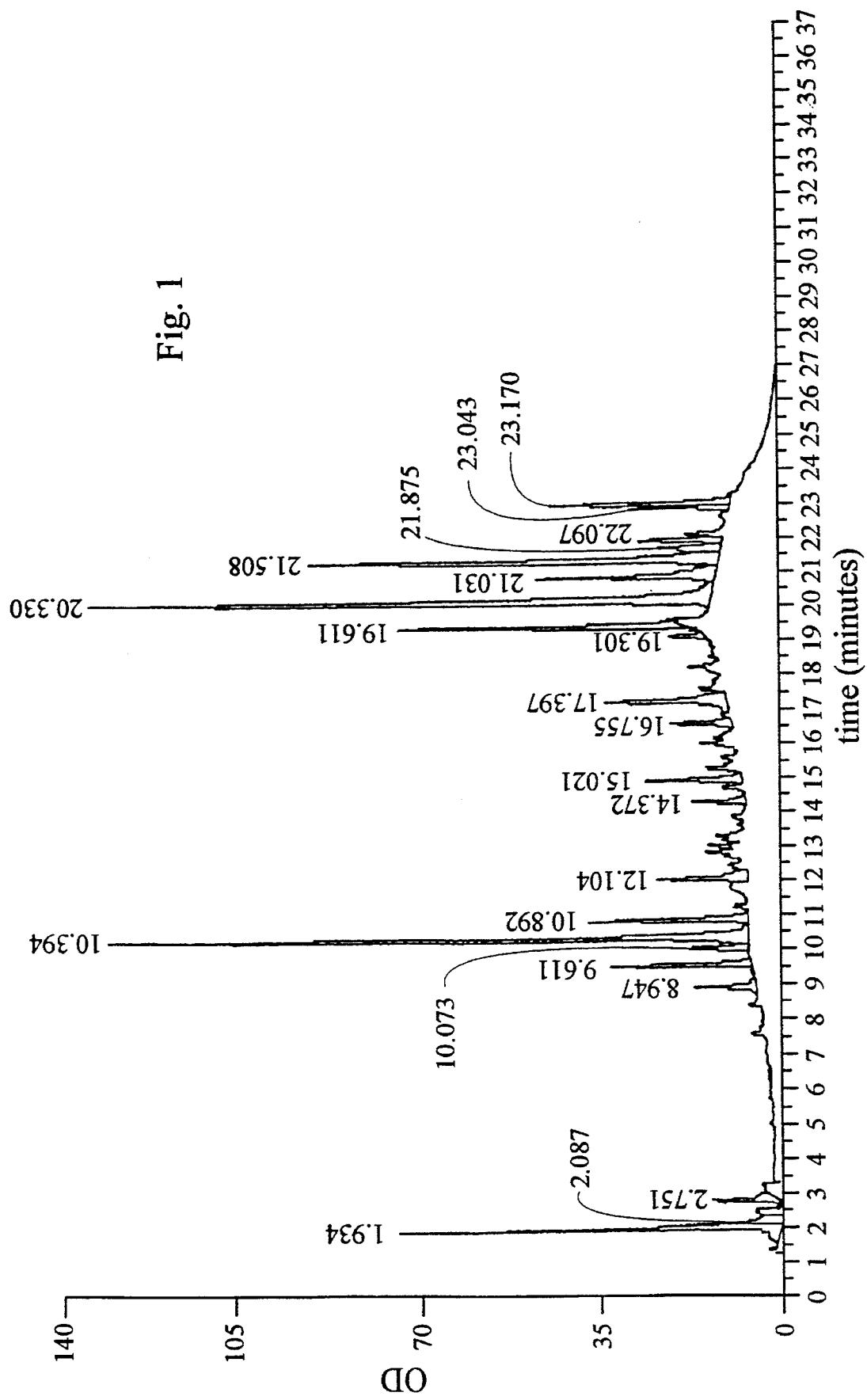
FIG. 1 shows a reverse phase High Pressure Liquid Chromatography (HPLC) separation/analysis of extensively oxidized β-carotene.

FIG. 1 presents a reversed phase High Performance Liquid Chromatography (HPLC) characterization of the oxidation mixture.

Figure 2:
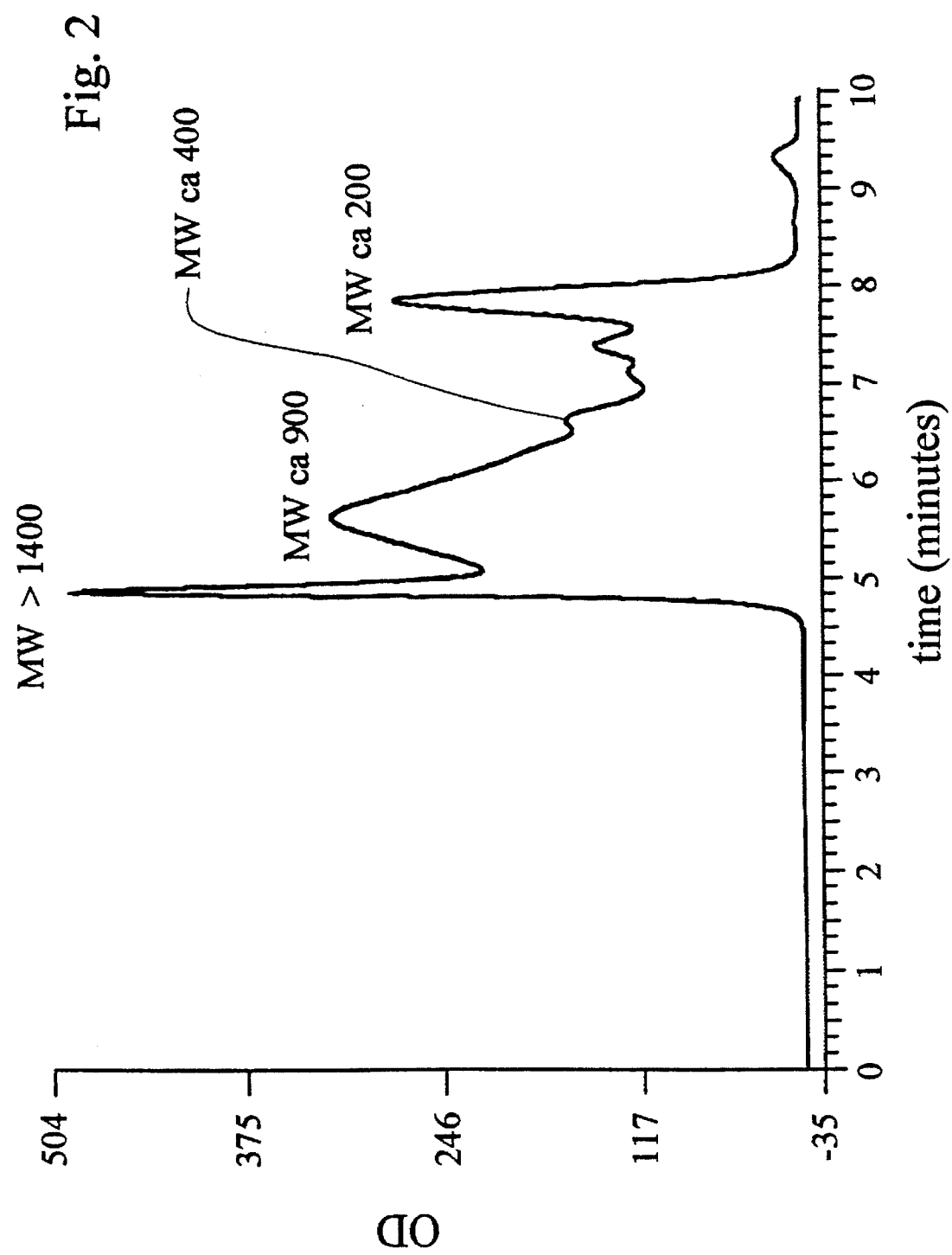
FIG. 2 illustrates the results of gel permeation chromatography (GPC) analysis of extensively oxidized β-carotene.

FIG. 2 presents a GPC characterization of the oxidation mixture showing, in arbitrary units, the composition of the oxidation mixture according to the molecular weight of the components. The molecular weight range is broadly distributed from about 600 to about 8000 Dalton with the maximum at about 900 Dalton (the sharp peak at 4.9 min. is an artifact, due to the nature of the GPC column, all the components of the mixture with molecular weight above ca. 1400 elute simultaneously).

Figure 3:
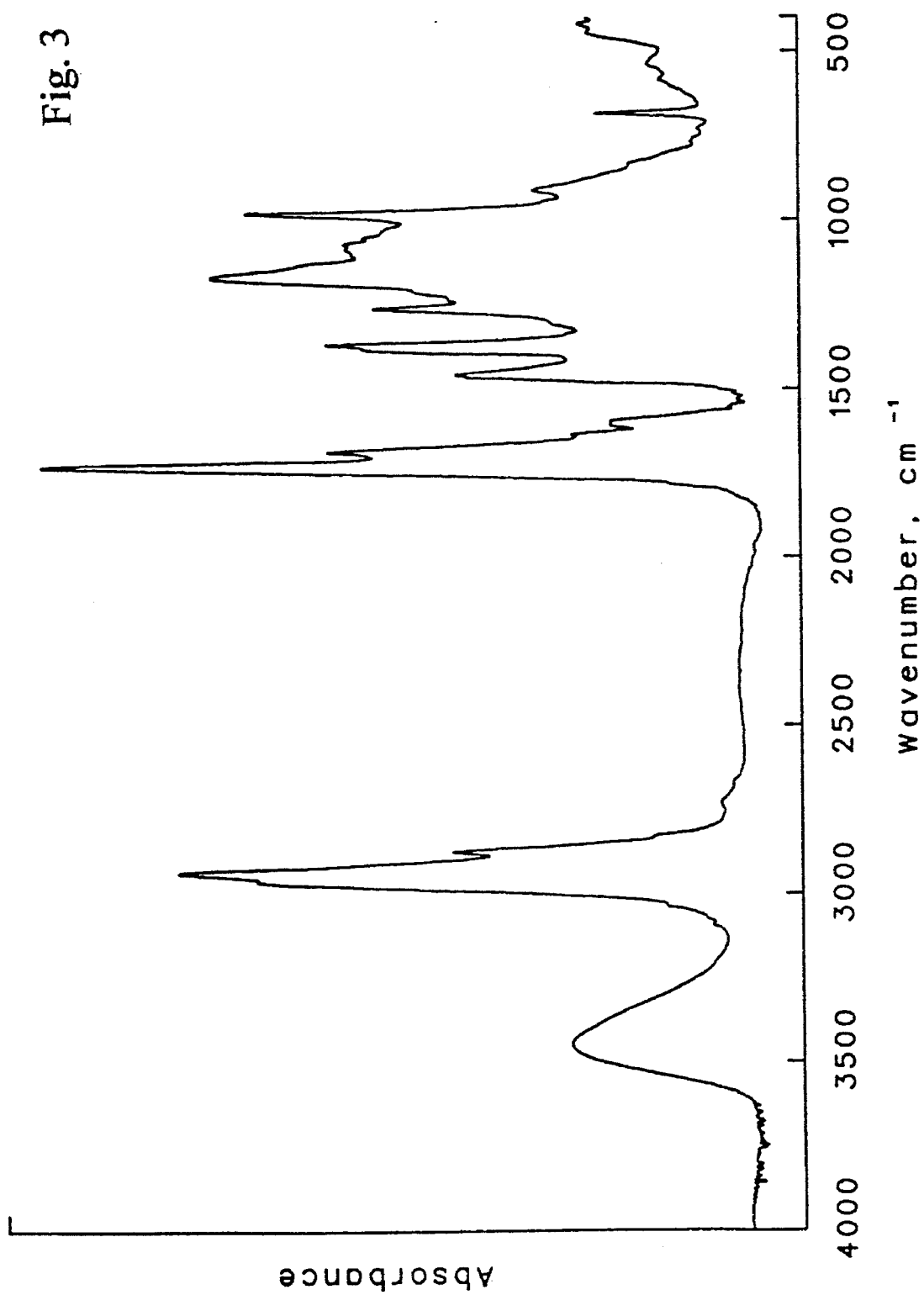
FIG. 3 represents Fourier Transformed Infrared (FTIR) spectrum of the oxidation mixture from extensively oxidized β-carotene.

FIG. 3 is a Fourier Transformed Infrared (FTIR) spectrum of the oxidation mixture.

Figure 4:
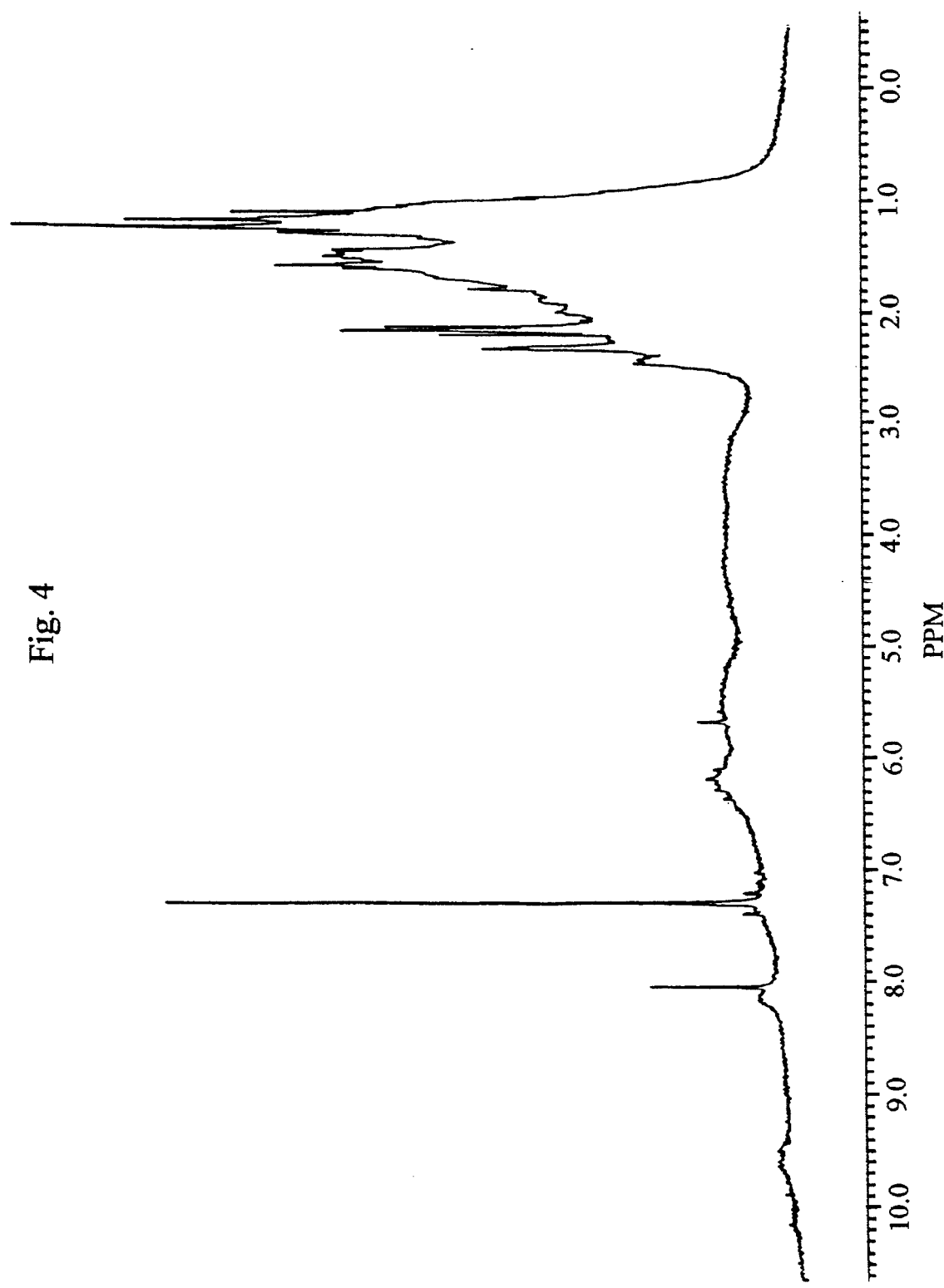
FIG. 4 represents a proton Nuclear Magnetic Resonance (NMR) spectrum of the oxidation mixture of extensively oxidized β-carotene.

FIG. 4 is a proton Nuclear Magnetic Resonance (NMR) spectrum of the oxidation mixture.

Partial Fractionation of the Mixture of Products from Extensively Oxidized b-Carotene:

An extensively oxidized mixture with no β-carotene remaining, obtained in solution, was fractionated by successive solvent precipitations. The fractions were characterized by gel permeation chromatography (GPC) and by elemental analysis. The results of elemental analysis and analysis of acid and peroxide content are shown in Table 1:

TABLE 1

Characteristics of various Fractions obtained by Successive Solvent Precipitations of Extensively Oxidized β-Carotene.

| Fraction | 1 | 2 | 3 | 4 |
|---|---|---|---|---|
| Weight % | 37 | 17 | 14 | 32 |
| Titratable acids [$10^{-4}$ mol/g] | 4.3 ± 0.3 | 4.3 ± 0.2 | 6.1 ± 0.3 | 6.2 ± 0.1 |
| Peroxides (iodometric) [$10^{-4}$ mol/g] | 9.5 ± 1.0 | 9.9 ± 0.8 | 8.2 ± 0.3 | 5.9 ± 0.4 |
| Peroxides (oxidation of $Fe^{2+}$) [$10^{-4}$ mol/g] | 8.3 ± 0.2 | 8.9 ± 0.2 | 8.8 ± 0.9 | 5.5 ± 0.1 |
| Elemental Analysis: | | | | |
| C | 58.5 | 58.7 | 61.2 | 65.3 |
| H | 7.2 | 7.0 | 7.6 | 8.7 |
| O | 34.3 | 34.3 | 31.2 | 26.0 |

Fractions were obtained in the following way:
the crude mixture (1.2 g) was dissolved in tetrahydrofuran (THF) (5 ml) and hexane (15 ml) was added slowly while the solution was vortex-mixed. The sample was centrifuged (3000 rpm, 3 min.) and the oily residue was separated, washed once with a mixture of THF and hexane (5:15) and dried under vacuum to yield fraction 1.
The remaining solution was combined with the liquid from the washing, evaporated and the residue dissolved in THF (3 ml). Precipitation with hexane (15 ml) followed by centrifugation and washing (THF/hexane, 3:15) gave fraction 2. As before, the remaining solution, combined with the Wash, was evaporated and dissolved in benzene (3 ml). Precipitation with hexane (15 ml) followed by washing (benzene/hexane, 3:15) gave fraction 3. The supernatant material was labelled as fraction 4.

Figure 5A:
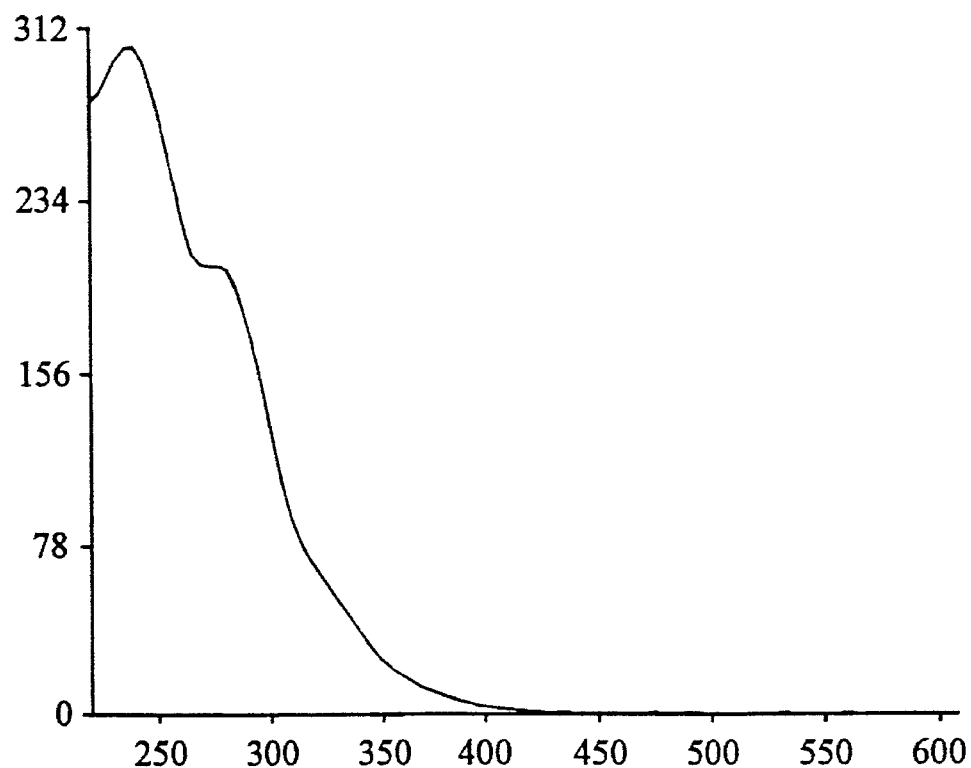
FIG. 5a represents the UV spectrum of the polymeric component of the oxidation mixture of extensively oxidized β-carotene (fraction 1)
Figure 5B:
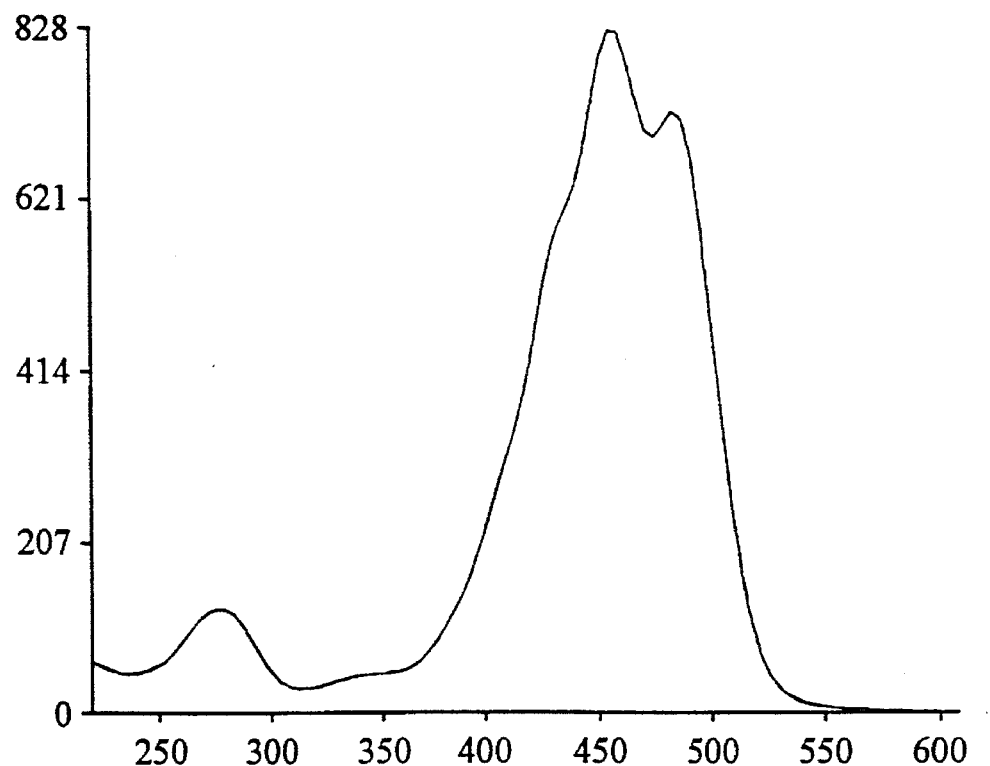
FIG. 5b represents UV spectrum of β-carotene.

It was estimated from the weights of the individual fractions and GPC traces that the polymeric material accounted for close to 90 wt. % of the mixture of products of the extensively oxidized -β-carotene. The percentage of oxygen in the first three fractions obtained (i.e., the majority of the product) reflects well the 6–8 molar equivalents of oxygen taken up by the β-carotene and the 30–35% net increase in weight accompanying formation of the products. Addition of 6–8 molecules of oxygen to β-carotene, originally comprised of 11 conjugated double bonds, implies loss of most of the system of conjugated double bonds as most of the double bonds will have been disrupted by the formation of new carbon-oxygen bonds. Thus, the ultra violet-visible absorption spectrum of the polymeric substances show maximum absorption at a much shorter wavelength (ca 240 nm with a shoulder at 280 nm) compared to the parent β-carotene (FIG. 5a and FIG. 5b correspondingly).

The polymeric material, which is soluble in THF, methanol, acetone and acetonitrile, is stable indefinitely below room temperature but partially decomposes under heating forming volatile products as found by way of gas chromatography.

The GPC analysis of the specific fractions, 1–4, of the oxidation mixture (FIGS. 6a–6d respectively), in comparison with FIG. 2, demonstrates that fractions 1 and 2 contain relatively large amounts of high-MW compounds while fractions 3 and 4, and particularly fraction 4, contain substantial amounts of low MW materials.

Oxidation of β-Carotene in Presence of Antioxidants

The oxidation of β-carotene (20 mM) also was carried out under the conditions described above but in the presence of 0.01 to 0.10 molar equivalents (with respect to β-carotene) of either alpha-tocopherol or 2,6-di-t-butyl- 4-methoxyphenol. The reaction was slowed down considerably (1 molar equivalent of oxygen was consumed in ca. 6 days). The oxygen uptake plot was linear. The slope of this line was independent of the inhibitor type and its concentration. The β-carotene consumption did not exceed 10% over a 6 day period.

Oxidation of β-Carotene in Presence of Free Radical Catalysts 2,2'-Azo-bis(2-methylpropionitrile) accelerated formation of reaction products.

Figure 6A:
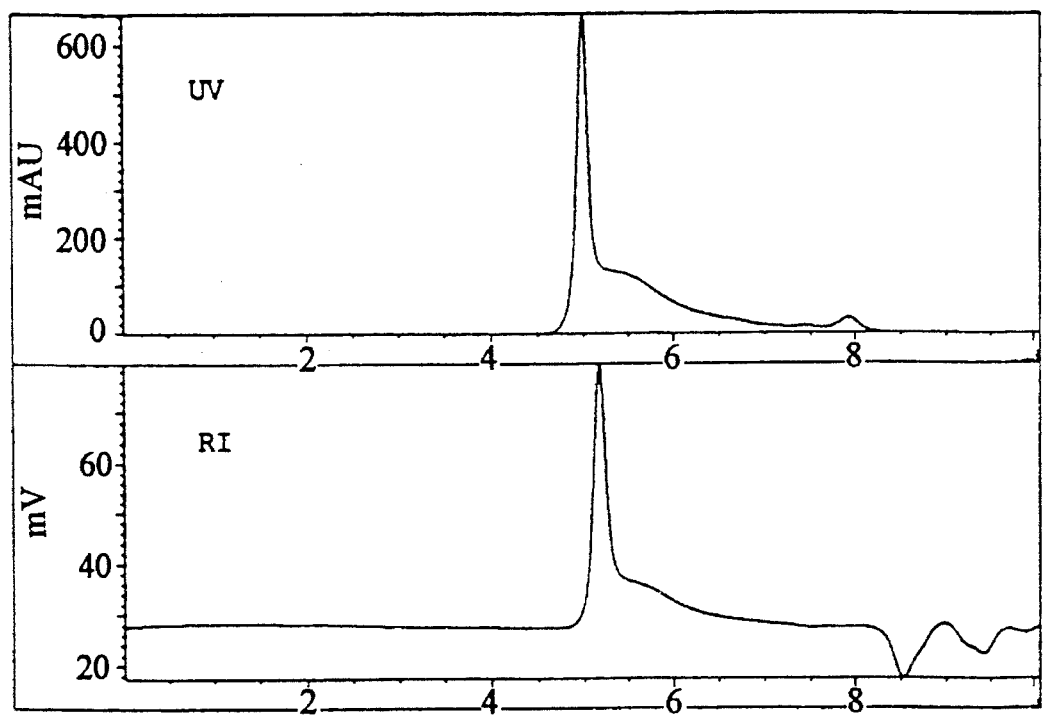
FIGS. 6a–6d illustrate the results of GPC analysis of specific fractions of the polymeric mixture as follows.
Figure 6B:
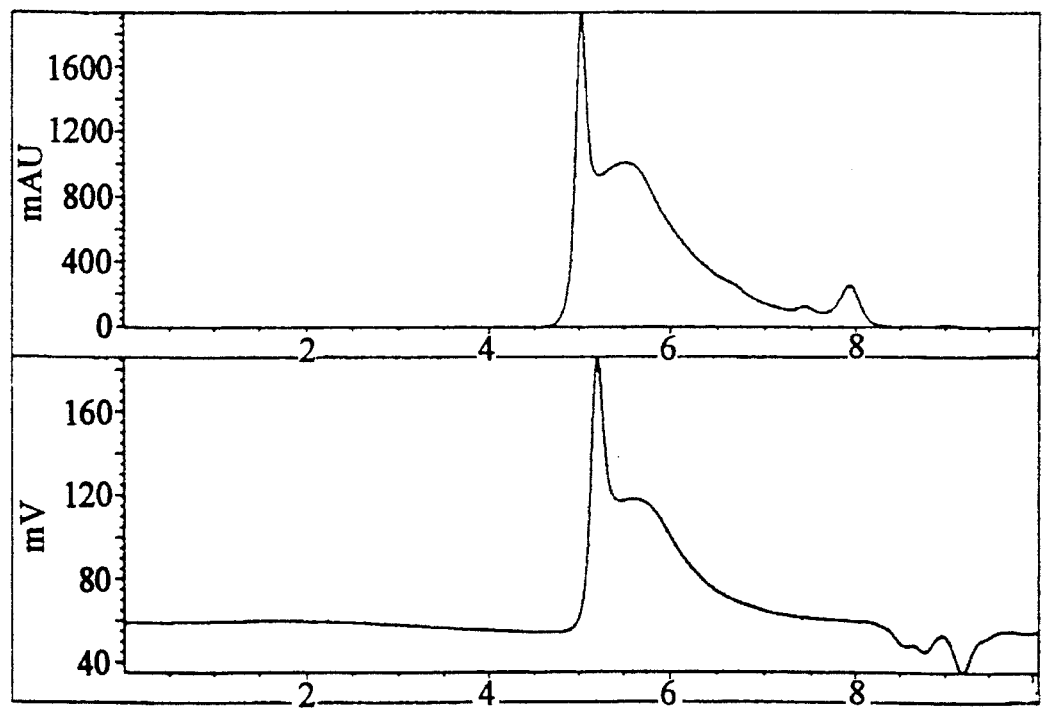
Figure 6C:
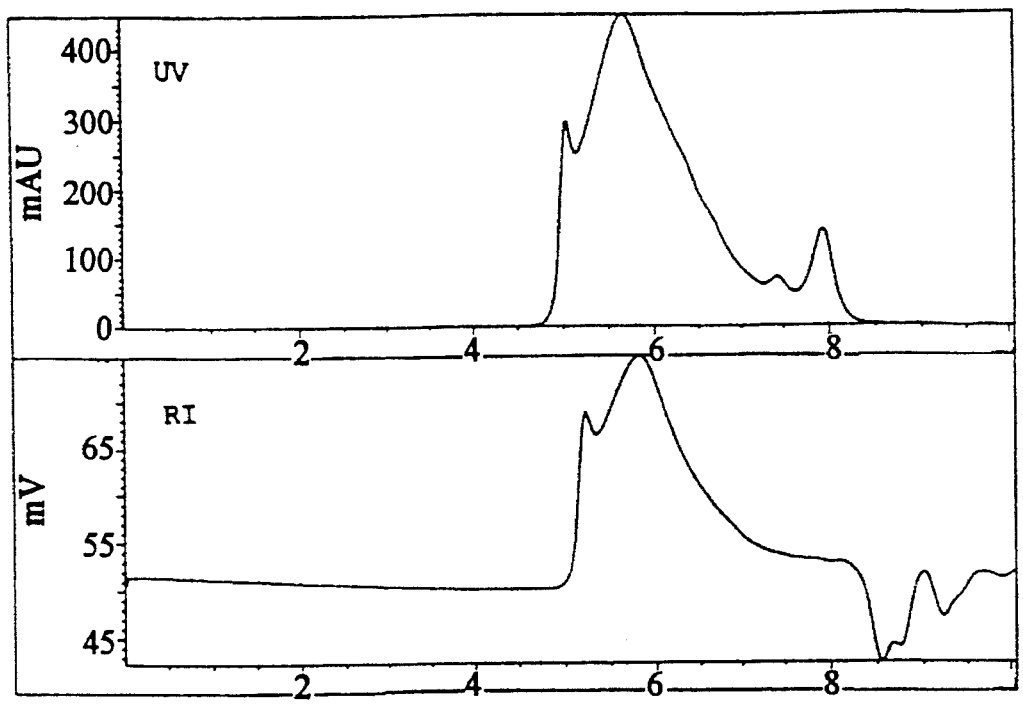
Figure 6D:
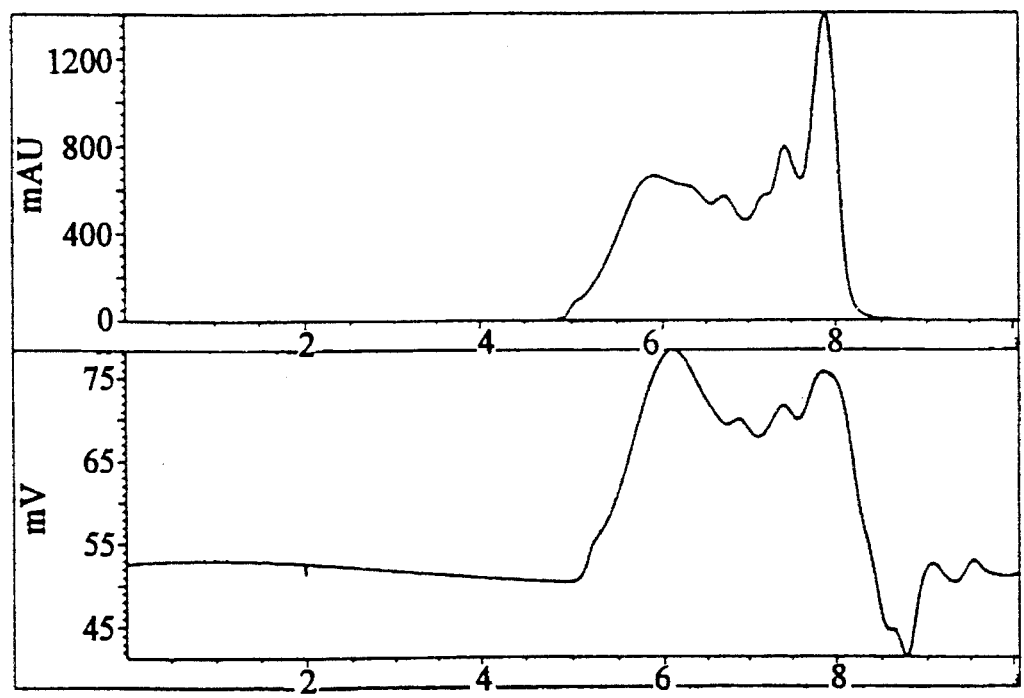

Solid State Oxidation of b-carotene:

A similar polymeric material was obtained as virtually the only product, as indicated by FTIR and GPC analysis, when pure, crystalline carotene was oxidized in the solid state. The reaction was carried out by allowing crystalline β-carotene to stand in air over a period of up to 8 weeks in an open, clear glass vessel with no attempt to exclude light during daylight hours. The reaction was considerably slower than the reaction carried out in solution (40 days vs. 3 days). The FTIR spectrum of the polymer obtained by oxidation of solid β-carotene (FIG. 8) and the FTIR spectrum of fraction 1 of the polymer obtained by oxidation in solution (FIG. 7) were clearly similar regarding the location and relative intensities of the absorption peaks. The same was true for the results of GPC analysis (FIG. 9 vs. FIG. 6a). Furthermore, the substances obtained by oxidation of β-carotene in the solid state, and from partial and extensive oxidation in solution displayed similar biological activities in inhibiting the proliferation of cancerous and transformed cells grown in culture.

Example 2: Oxidation of canthaxanthin

Canthaxanthin was oxidized under conditions identical to those used for the oxidation of β-carotene. Thus, a 20 mM solution of canthaxanthin (Fluka) in benzene saturated with oxygen was incubated in a shaker bath, in the dark, at 30° C. under pure oxygen at atmospheric pressure. After 190 hours, when ca. 7 molar equivalents of oxygen was consumed, the solvent was evaporated to give a resin-like, yellow residue. Thus, although the reaction was slower, again there was very extensive reaction with oxygen. GPC analysis of the oxidation mixture (data not shown) indicated strong similarities with extensively oxidized β-carotene, i.e., the reaction products were predominantly polymeric substances.

Example 3: Oxidation of retinoic acid

Reaction of retinoic acid with oxygen under the conditions used for β-carotene and canthaxanthin proceeded very slowly. The reaction was accelerated by carrying it out at elevated pressure.

Retinoic acid (Sigma) dissolved in benzene (0.5 ml; 20 mM) in a glass test tube was placed in a high pressure apparatus constructed of INCONEL 600. The apparatus was pressurized to 300 psi oxygen and placed for 3 days in a temperature-controlled bath set at 42° C. HPLC analysis of the reaction mixture showed that the reaction was incomplete. Reaction was continued for a further 2 days under the same conditions, except that the temperature was increased to 50° C., for a total reaction time of 5 days. Very little unoxidized retinoic acid remained (less than 1% of the total product). GPC analysis (data not shown) indicated the presence of higher MW products which, however, represented a much smaller fraction of the total reaction product than was found for β-carotene and canthaxanthin, and the absence of detectable material with MW greater than the cut-off of the column (approximately 1400 Dalton).

Biological Activity

In vitro biological assays were carried out by testing for antiproliferative activity, induction of differentiation, and activity against tumorigenic viruses in various cultured cell lines. Most of the results were obtained for extensively oxidized β-carotene but also include some results for extensively oxidized canthaxanthin and retinoic acid.

In vivo tests were carried out by testing extensively oxidized β-carotene and canthaxanthin for:
toxicity in mice;
inhibition of growth of tumors in mice including histopathological examination of tumor changes (tumor derived from a transplanted, chemically-induced rat mammary cancer cell line).

In vitro tests

In order to determine the biological properties of the mixture of the invention, oxidized β-carotene was tested in vitro for anti-proliferative effects, antimitotic properties and induction of differentiation. Retinoic acid and/or β-carotene were used as controls in some of the cell lines tested in order to differentiate their effects from that of oxidized β-carotene. The influence of oxidized β-carotene on the cell cycle was also studied. All concentrations relating to activity are expressed in micro molar equivalents of β-carotene.

Cell Models: Cell lines and characteristics

A variety of cell lines were used to test the effect of oxidized β-carotene on proliferation and/or differentiation. The lines are either established transformed cell lines or are isolated from tumors of patients suffering from cancer. In addition, two murine cell lines were used in which the cellular differentiation program is well defined with appropriate protein markers. For these two lines, matching clones transfected with the human papilloma virus type 16 (HPV16)—a virus associated with cervical cancer—have been characterized and shown to exhibit transformation. The transformed phenotypes L6-HPV16 (derived from L6 cells) and BALB/c/MK-HPV16 (derived from BALB/c/MK cells) have been characterized by their hormone independence and ability to form colonies on soft agar.

The pattern of expression of the virus proteins in biopsies obtained from patients with severe neoplasia was established in our laboratory using the reverse transcriptase polymerase chain reaction (RT-PCR). In the biopsied material, the pattern of expression is similar to that of the transformed L6 clone, demonstrating the relevance and validity of the L6 model for testing purposes.

The BALB/c/MK cell line is of interest since it differentiates upon exposure to high concentrations of $Ca^{2+}$ ions.

When cells are exposed to low calcium, they revert to their pre-differentiation state in less than 72 hr.

The differentiation inducing properties of oxidized β-carotene were further investigated in two additional models which used mouse embryonic stem cells (i.e., a quasi normal cell line) and several animal and human neuroblastoma cell lines (i.e., cancerous cells).

Embryonic stem (ES) cells are totipotent, i.e., they can give rise to any cell lineage of the organism. In vitro, under certain conditions, they differentiate spontaneously into a variety of mixed types. Treatment with substances known to promote differentiation directs ES cells towards a single phenotype. For example, retinoic acid prompts ES cells cultured under conditions established at the National Research Council to differentiate into neurons (unpublished data).

Murine Cell Models

1a. L6 rat primary myoblasts (L6).
1b. L6 cells transfected with human papilloma virus type 16 (L6-HPV).
2a. Mouse BALB/c/MK keratinocytes (BALB/c/MK).
2b. Mouse BALB/c/MK transfected with human papilloma virus type 16 (BALB/c/MK-HPV16).
3a. Mat B-WT: rat mammary adenocarcinoma.
3b. Mat B-MLNr rat mammary adenocarcinoma resistant to melphalan.
3c. Mat B-DOXr rat mammary adenocarcinoma resistant to adriamycin.
4. B16 mouse melanoma.
5. DA-3 mouse mammary carcinoma induced by DMBA.
6. FDCP-1 Mouse myeloid leukemia.

The two cell lines, Mat B MLNr and Mat B-DOXr exhibit multidrug resistance; Mat B-WT is the wild type. They are poorly differentiated cells which do not express estrogen or progesterone receptors.

Human Cell Models

7a. MCF7-WT human breast carcinoma.
7b. MCF7-ADRr human breast carcinoma resistant to adriamycin.

The cells are moderately differentiated and positive for estrogen and progesterone receptors.

8a. Uro 9 human urothelial carcinoma; well differentiated.
8b. Uro 10 human urothelial carcinoma; poorly differentiated.
9. L14 human lung adenocarcinoma; moderately differentiated (isolated in-house at the Lady Davis Institute of the Montreal Jewish Hospital from a patient tumor).
10. NB4 Human acute promyelocytic leukemia.

Anti-Proliferative Effect

Table 2 summarizes the results obtained with the MTT viability/toxicity assay from Promega (a metabolic test based on mitochondrial dehydrogenase activity). Viability was assessed at increasing concentrations (multiples of 2.5) of oxidized β-carotene. The doses which halve the growth of the cell population, as compared to untreated controls, are reported as IC 50 values.

TABLE 2

Anti-Proliferative Effect of Extensively Oxidized β-Carotene

| Cell Lines | Origin | IC 50 [μM] |
| --- | --- | --- |
| MatB-WT | Rat mammary adenocarcinoma | 25.5 |
| Mat-MLNr | | 21.0 |
| B16 | Mouse melanoma | 12.4 |
| DA-3 | Mouse mammary carcinoma | 15.6 |
| FDCP-1 | Mouse myeloid leukemia | 7.5 |
| L6 | Rat embryonic myoblasts | 51.9 |
| L6-HPV16 | | 28.2 |
| MCF7-WT | Human breast carcinoma | 11.3 |
| MCF7-ADRr | | 11.3 |
| Uro-9 | Human urothelial carcinoma | 17.7 |
| Uro-10 | | 19.8 |
| L14 | Human lung adenocarcinoma | 18.5 |
| NB4 | Human promyelocytic leukemia | 4.8 |

Exponentially growing cells cultured at low density (1E4 to 1E5 cells/1–5 ml) were exposed to a single dose of different concentrations of extensively oxidized β-carotene for 72 hr or more. Cell growth was determined by the MTT test. IC 50 values (expressed in β-carotene equivalents) were determined graphically from survival curves (plots of cell growth versus concentration of oxidized β-carotene).
Each value in the Table 2 corresponds to an average of at least two independent experiments. Different batches of extensively oxidized β-carotene were tested and gave consistent results. Note the sensitivity of the NB4 leukemia cell line and the lack of activity on the L6 control cells.
Retinoic acid and β-carotene (each 3 μM), used as controls for some cell lines, were found to have no effect on the cell growth curves, except for NB4 cells which responded to retinoic acid.

As a cross-check on the use of the MTT test, IC 50 results for L6 and L6-HPV16 cell lines were confirmed by cell enumeration using a Coulter counter as illustrated in Table 3.

TABLE 3

Comparison of the anti-proliferative effect (IC 50 [μM]) as measured by MTT test and cell enumeration by Coulter counter

| Cell Line | MTT | Coulter counter |
| --- | --- | --- |
| L6 | 51.9 | 39.0 |
| L6-HPV16 | 28.2 | 24.6 |

The fractions obtained from extensively oxidized carotene after successive organic solvent precipitations were assayed on the MCF7-WT cell line; two fractions, 1 and 3 were found to be considerably more active than the crude mixture, as illustrated in Table 4.

TABLE 4

Anti-proliferative activity of fractions against MC7-WT cell line (mM)

| Fractions mixture | 1 | 2 | 3 | 4 | crude |
| --- | --- | --- | --- | --- | --- |
| MCF7-WT IC 50 | 11.8 | 17.3 | 13.1 | 26.2 | 22.8 |

Cells were treated as described in the footnote to Table 2.

Although normal cells appear to be mildly inhibited, over a longer period of time in culture this effect gradually disappeared, showing that extensively oxidized β-carotene does not drastically affect normal cells. This would potentially allow cancer patients to be treated repeatedly with limited side effects.

Effect on Cell Differentiation

Morphological Observations on the L6 myoblast models:

The cultured rat myoblasts, L6, are capable of differentiation in vitro. At the National Research Council, five steps have been characterized in the differentiation program of these cells using morphometry, in situ immunofluorescence and flow cytometry analysis.

The known markers (characteristic proteins) of myocyte differentiation used were: fibronectin, a-actin, N-CAM, vimentin and expression of acetylcholine receptors. In addition, it was demonstrated that acetylcholine receptors specific to the prefusion stage were not expressed in the L6-HPV16 cells. Five stages were identified, the phenotypes of which in order of increasing differentiation are described below:
1. Cells have embryonic fibroblast-like appearance.
2. Cells acquire a bipolar morphology.
3. Cells become oriented.
4. Cells enter pre-fusion stage.
5. Cells show formation of syncitium and myotubes.

It has been found that the HPV16 transfected cells are transformed and blocked at the pre-fusion stage. That is, HPV16 transfected cells are blocked at stage 4. Upon treatment with extensively oxidized β-carotene, however, better orientation of the cells was observed and some syncitium formation was initiated, corresponding to partial entry into stage 5 of differentiation.

Culturing in media differing in their calcium content showed that oxidized β-carotene was more potent on both controls and transfected cells when the media were poor in calcium (0.05 mM). In addition, an antagonism was observed between calcium and oxidized β-carotene in the expression of differentiation markers reported above. This prompted some exploratory experiments on the effects of calcium upon the cells treated with extensively oxidized β-carotene. The myoblast and keratinocyte models were used.

Briefly, in L6 myocytes, the influx of exogenous calcium in the cells occurs via nonspecific cationic channels (as we have established earlier and in agreement with existing literature). Inside the cells, the level of calcium is controlled by calcium release from internal stores. In addition, an acetylcholine receptor expressed at the pre-fusion stage of the L6 differentiation program modulates sarcoplasmic calcium channels.

In keratinocytes, the nature of the channels regulating calcium entrance and release from stores is not yet elucidated.

Experiments were conducted by two techniques: electrophysiology and imaging using Fura-2. Preliminary results indicate that extensively oxidized β-carotene acts as a calcium channel blocker or calcium chelator. This was confirmed by its ability to partly overcome multidrug resistance in the multidrug resistant cell lines described. This, however, appears less effective than conventional channel blockers like verapamyl.

Pattern of the Differentiation Markers in the BALB/c/MK models

In BALB/c/MK keratinocytes, cytokeratins 1, 5 and 10, as defined in the Poll catalogue, were first identified by Western immunoblot. Cytokeratins 1 and 10 are known to be associated with higher levels of differentiation while cytokeratin 5 is associated with less differentiated, still proliferating cells.

Flow cytometry analysis showed that cytokeratins were generally less expressed in untreated HPV16 transfected cells than in untreated matching control cells.

Cytokeratin 5

Exposure to 1.8 mM calcium, which induces irreversible differentiation within 3 days, resulted in an increase in the expression of cytokeratin 5 in the controls and the transformed cells. Exposure to extensively oxidized β-carotene resulted in a similar effect except that 6 days of exposure were sufficient to induce expression in the controls, while 9 days were necessary for the transformed cells.

Exposure to both inducers simultaneously, cancelled the enhancement of expression, showing that the two compounds are antagonistic.

Cytokeratins 1 and 10

A striking increase in expression of both of these cytokeratins upon exposure to increased calcium (from 0.05 mM to 1.8 mM) was observed in control cells while the transformed cells did not show any response.

In contrast, extensively oxidized β-carotene induced expression of both markers in both lines. As with the L6 line, longer exposure was required for a response from BALB-HPV16 as compared to controls.

Again, antagonism with calcium treatment was observed. These results seem of real importance because they provide evidence that, at least in the keratinocyte model, extensively oxidized β-carotene enhances differentiation in the HPV16 transformed cells whereas the classical calcium cell differentiation inducer is ineffective.

Induction of differentiation by extensively oxidized β-carotene (estimated by morphological criteria) also has been observed in the NB4 promyelocytic leukemia cell.

ES and neuroblastoma cells

Under conditions similar to those developed at the National Research Council for the induction of differentiation by retinoic acid of ES cells into neurons, oxidized β-carotene also promotes the differentiation of ES cells into neural cells as shown in FIG. 10 and as assessed by specific markers, using immunohistochemical techniques. However, there are two significant differences between the effect of retinoic acid and oxidized β-carotene on ES cells.
1) Retinoic acid promotes ES cell differentiation into 80% of a bipolar phenotype in a dose-independent fashion in 0.1 to 1 μM range (FIG. 10b) while oxidized β-carotene, at the optimal concentration (7.5 μM β-carotene equivalents), elicits terminal differentiation into ca. 90% of highly branched phenotypes resembling Purkinje cells (FIG. 10d); the mechanism of high branching is not yet fully elucidated.
2) The induction of terminal differentiation is kinetically different for the two inducers; oxidized β-carotene is far more effective than retinoic acid (15 hr versus 3 days, respectively, under our experimental conditions)

In the neuroblastoma cell lines Neuro2A, IMR32, SK-N-SH and SK-N-MC oxidized β-carotene promoted similarly striking high degrees of differentiation, whereas retinoic acid evoked only partial differentiation.

The results from the ES and neuroblastoma models indicate that oxidized β-carotene is a powerful differentiation promoter and it appears that its mechanism of action is different from that of retinoic acid.

Activity against expression of tumorigenic viral genes

The observation that extensively oxidized β-carotene may possess activity against the expression of tumorigenic viral genes relies on three independent experiments.

Cytopathy: The symptoms of viral infection, clearly visible as intense vacuolization around the nuclei of the transfected cells L6-HPV16 and BALB/c/MK-HPV16, drastically decreased or disappeared upon exposure to oxidized β-carotene.

Messenger RNA was extracted from transfected cells that have and have not been exposed to the extensively oxidized β-carotene. The kinetics of the expression pattern of the viral gene products has been analyzed by RT-PCR. Initial results showed that the pattern of expression of the viral proteins and the myc oncogene (an oncogene related to proliferation) was different for cells treated with oxidized β-carotene, compared to those treated with retinoic acid or β-carotene.

A monoclonal antibody raised against a fragment common to the E6 and E7 oncogenic proteins of HPV16 was used to determine the expression of both proteins using polyacrylamide gel electrophoresis, Western blot analysis and flow cytometry. A decrease of the expression of E6 and E7 proteins was observed after 9 to 12 days exposure of the virus transfected cells to oxidized β-carotene.

Effect of oxidized β-carotene on the cell cycle

One of the most striking effects of oxidized β-carotene on transformed or cancerous cells is that it limits proliferation. This implies that cycling of the cell population is either blocked or slowed down. Four different cell lines, two myoblast lines (L6 and L6/HPV16) and two leukemia lines (human NB4 and mouse FDCP-1) were investigated using flow cytometry in association with the visualization agent, propidium iodide (a compound that binds to nuclear DNA). In all cases, a progressive accumulation of the cells in the G1 and S phases of the cell cycle was observed. This effect was particularly visible during the logarithmic growth phase of the proliferating leukemia cell lines, which grow in suspension. The effect was also clear with the myoblast lines, in spite of the limitation of growth resulting from the well known contact inhibition that occurs in adhesive cell cultures. It is clear that the relative increase of the G1 cell population reflects the fact that the cell cycle is blocked or dramatically slowed down during the S phase, resulting in a large accumulation of cells first in the S phase, then in the G1 phase, because the rest of the cell cycle is also slowed down.

Anti-proliferative activity of incompletely oxidized β-carotene, antioxidant-inhibited β-carotene oxidation mixture, and extensively oxidized canthaxanthin and retinoic acid:

Table 5 shows the relative antiproliferative effects towards the MC7-WT cell line of incompletely oxidized β-carotene containing both the polymeric oxidation product and unreacted β-carotene, the oxidation products obtained from the oxidation of β-carotene inhibited by a-tocopherol (5 mole %), fully oxidized canthaxanthin and retinoic acid (syntheses described above). All of the samples contained at least some of the higher MW oxidation materials and all showed considerable anti-proliferative activity.

TABLE 5

Anti-prolif orative activity against MC7-WT cell line of partially oxidized β-carotene, products obtained in inhibited oxidation of β-carotene, as well as extensively oxidized canthaxanthin and retinoic acid

| Sample | IC 50 (mM) |
| --- | --- |
| ca. 25% Oxidized β-carotene | 22 |
| ca. 50% Oxidized β-carotene | 21 |
| 100% oxidized β-carotene | 17 |
| a-Tocopherol-retarded oxidation of β-carotene | 11 |
| Oxidized canthaxanthin | 9 |
| Oxidized retinoic acid | 7 |

Cells were treated as described in the footnote to Table 2.

In Vivo Study of Toxicity and Anti-Tumor Activity of Extensively Oxidized β-Carotene Assessment of Toxicity: extensively oxidized β-carotene and canthaxanthin Toxicity was assessed by monitoring body weight of female BALB/c mice and by general examination of the animal. Dosages of 5 mg/kg and 10 mg/kg were injected intraperitoneally on days 1, 3 and 5 (Table 6). The control groups received solvent only (20% aqueous ethanol). A similar study was carried out using 50 and 100 mg/kg injections on days 1,3,5,8 and 11. No overt toxic effects were observed (data not shown).

Extensively oxidized B-carotene is non-toxic to healthy mice even when applied in six doses of 100 mg/kg. It should be stressed that even with repeated doses (9 times) of up to 150 mg/kg (with tumor bearing mice), no adverse effects have been observed.

Similarly, extensively oxidized canthaxanthin showed no overt signs of toxicity under an identical dose/injection pattern regime (data not shown).

TABLE 6

Effect of extensively oxidized β-carotene on body weight of mice

| | Average Body Weight [g] | | |
| --- | --- | --- | --- |
| Day | Control | 5 mg/kg | 10 mg/kg |
| 1 | 14.0 | 14.4 | 14.0 |
| 2 | 14.0 | 14.5 | 14.0 |
| 5 | 14.4 | 14.9 | 14.5 |
| 7 | 14.8 | 15.3 | 14.6 |
| 9 | 15.2 | 15.8 | 15.2 |
| 11 | 15.7 | 16.3 | 15.7 |
| 13 | 16.1 | 16.7 | 16.2 |
| 15 | 16.6 | 17.3 | 16.9 |
| 17 | 17.1 | 17.7 | 17.4 |
| 19 | 17.6 | 18.3 | 17.9 |
| 21 | 18.1 | 18.7 | 18.4 |
| 23 | 18.7 | 19.4 | 19.1 |
| 25 | 19.2 | 20.0 | 19.8 |

Anti-Tumor Activity: Tumor Model System

The mouse D1-DMBA-3 (DA-3) mammary adenocarcinoma model was used. The cell line was derived from BALB/c mice bearing an immunogenic non-metastatic, murine mammary adenocarcinoma induced by 7,12-dimethylbenzanthracene (DMBA).

One million DA-3 cells were injected subcutaneously into each female BALB/c mouse. When the tumors became palpable (0.5 cm diameter, 1–2 weeks) the animals were randomized into groups and injected intraperitoneally with the oxidized β-carotene at dosages ranging from 5 mg/kg up to 150 mg/kg. Tumor growth was measured every 2–3 days. The evaluation was carried out by determining inhibition of tumor growth by measuring tumor volume as a function of time, as described by Alaoui-Jamali et al., in J. Pharmacol. Exp. Ther. 1993, 264 (3), 1299. Again, the control group received solvent only (20% aqueous ethanol).

FIG. 11 and FIG. 12 illustrate the effect of extensively oxidized β-carotene on tumor growth. FIG. 11 corresponds to a dose of 10 mg/kg injected on days 0,2,4,7,9,11,14,16 and 18. FIG. 12 corresponds to a dose of 150 mg/kg injected in the same way.

For histological examination, a few, randomly chosen animals were sacrificed and tumors were dissected and fixed in 10% formalin in normal saline. Histological sections were prepared from each of the formalin-fixed, paraffin-embedded tumors and stained with hematoxylin-eosin.

Extensively oxidized β-carotene has a growth-retarding effect on a cancer cell-derived tumor implanted in mice. FIGS. 11 and 12 show that extensively oxidized β-carotene as applied repeatedly at dose as low as 10 mg/kg has the ability to effectively arrest the growth of the tumor and stabilize it for a long period of time.

FIG. 13a and FIG. 13b show the comparison of tumors in sacrificed animals which had been treated with different doses of extensively oxidized β-carotene and the control (untreated animal). In some animals hemorrhaging occurred around the tumors (FIG. 13b). In these cases the actual tumor size is smaller than when measured with calipers (the discrepancy is attributed to hemorrhagic swelling increasing the apparent tumor size).

Histopathological examination of tumors removed from treated animals revealed that:

oxidized β-carotene induces pronounced histological alterations, reflecting tissue death in DA-3 tumors.

tumor tissues showed many features of cell/tissue differentiation.

hemorrhagic areas are present in all treated tumors and are associated with extensive pigmentation and necrosis.

the pigments are not iron (iron staining using Prussian blue was negative), but may be hemosiderin probably resulting from hemorrhagia. It appears unlikely that the pigment is melanin. The exact nature of the pigmentation remains to be confirmed.

There was no evidence of similar histopathological changes in normal, non-tumor tissues.

As multiple intraperitoneal injections of the oxidized β-carotene mixture are well tolerated, even at concentrations of up to 150 mg/kg, the therapeutic index of oxidized β-carotene appears to be very high, which potentially offers a major advantage over traditional anti-cancer drugs.

To summarize, β-Carotene and canthaxanthin, as representative carotenoids, and to a lesser extent, retinoic acid, a representative retinoid, can undergo extensive oxidation to yield substances, insofar as oxidized β-carotene is a model, which demonstrate properties that make the substances useful as non-toxic agents active against cell proliferation, tumors, and tumorigenic viruses, and useful as promoters of cell differentiation. It is evident from chemical analysis of the highly oxidized β-carotene product mixture that none of the various forms of vitamin A are present or are present only in minor amounts. Furthermore, the biological activities of oxidized canthaxanthin and retinoic acid, which cannot form, vitamin A, indicate the presence of active substances that are different from vitamin A. Although the anti-proliferative and differentiation promotion activities of oxidized β-carotene resemble those of vitamin A itself, generally the effects are more powerful for oxidized β-carotene in a wide variety of circumstances. Also, there is the very important difference that oxidized β-carotene is non-toxic.

We claim:

1. A carotenoid, retinoid or related conjugated polyene derived oxidized mixture, useful as non-toxic cell differentiation inducer, anti-proliferative agent, and anti-tumor agent, that is formed upon reaction of a carotenoid, retinoid or related conjugated polyene compounds with oxygen wherein the consumption of oxygen is several-fold greater, on a molecular basis, than the amount of carotenoid, retinoid, or related conjugated polyene compound consumed.

2. A carotenoid, retinoid or related conjugated polyene derived oxidized mixture as defined in claim 1, obtained by oxidation in an organic solvent.

3. A carotenoid, retinoid or related conjugated polyene derived oxidized mixture as defined in claim 1, obtained by oxidation in the solid state.

4. The mixture of claim 1 derived from a retinoid or retinoic acid, wherein the oxidation is carried out under increased oxygen pressure.

5. A carotenoid, retinoid or related conjugated polyene derived oxidized mixture as defined in claim 1, obtained in the absence of catalysts or inhibitors of oxidation.

6. A carotenoid, retinoid or related conjugated polyene derived oxidized mixture as defined in claim 1, useful against the proliferative and differentiation-blocking effects of viral genes expressed in mammalian cells.

7. A polymeric component of the carotenoid, retinoid or related conjugated polyene derived oxidized mixture of claim 1.

8. A method of preparing a carotenoid, retinoid or related conjugated polyene derived oxidized mixture according to claim 1, the method involving reaction with oxygen, of a carotenoid, retinoid or related conjugated polyene compounds in an organic solvent or in the solid state, and involving the consumption of an amount of oxygen that is several-fold greater, on a molecular basis, than the amount of carotenoid, retinoid, or related conjugated polyene compound consumed.

9. The method according to claim 9 wherein the reaction with oxygen is carried out with β-carotene, retinoic acid or canthaxanthin in an organic solvent.

10. The method according to claim 9 wherein the reaction with oxygen is carried out with solid β-carotene, canthaxanthin or retinoic acid.

11. A method of treating a tumor in an animal or human, comprising administering to the animal or human in need thereof an effective amount of the mixture of claim 1.

* * * * *